United States Patent [19]

Bohn et al.

[11] Patent Number: 5,556,528
[45] Date of Patent: Sep. 17, 1996

[54] STRUCTURES WITH FIELD RESPONSIVE PERMEATION CONTROL

[75] Inventors: Paul W. Bohn, Champaign; Wenyuan Lu, Urbana, both of Ill.

[73] Assignee: Biotechnology Research & Development Corporation, Peoria, Ill.

[21] Appl. No.: 240,244

[22] Filed: May 10, 1994

[51] Int. Cl.$^6$ .................... G01N 27/26; G01N 27/447
[52] U.S. Cl. .................... 204/600; 204/450; 204/518; 204/627
[58] Field of Search .................... 204/299 R, 193, 204/301, 180.1, 600, 450, 518, 627

[56] References Cited

U.S. PATENT DOCUMENTS

| | | | |
|---|---|---|---|
| 4,931,328 | 6/1990 | Swedberg | 204/601 |
| 5,017,540 | 5/1991 | Sandoval et al. | 502/158 |
| 5,085,749 | 2/1992 | Grimshaw et al. | 204/180.1 X |
| 5,114,768 | 5/1992 | Swedberg | 428/36.91 |
| 5,180,479 | 1/1993 | Rose | 204/603 |
| 5,234,566 | 8/1994 | Osman et al. | 204/403 |
| 5,284,471 | 2/1994 | Sage, Jr. | 604/20 |
| 5,288,289 | 2/1994 | Haak et al. | 604/20 |
| 5,290,240 | 3/1994 | Horres, Jr. | 604/313 |
| 5,293,261 | 3/1994 | Shashidhar et al. | 359/87 |
| 5,298,139 | 3/1994 | Huang et al. | 204/603 |

OTHER PUBLICATIONS

Bohn, "Aspects of Structure and Energy Transport in Artificial Molecular Assemblies," *Annu. Rev. Phys. Chem.*, 44:37–60 no month available (1993).

Evans et al., "Characterization of an Aggregate–Sensitive Single–Component Energy–Transfer System," *J. Amer. Chem. Soc.*, 115:3306–3311 no month available (1993).

Evans et al., "The Influence of Molecular Orientation and Proximity on Spectroscopic Lineshape in Organic Monolayers," submitted to *J. Phys. Chem.* no date available.

Song et al., "Spectroscopic Characterization of Aggregation Behavior in Hemicyanine Dye Monolayer and Multilayer Systems," *J. Phys. Chem.*, 97:13736–13741 no month available (1993).

Okahata, "Lipid Bilayer–Corked Capsule Membranes. Reversible, Signal–Receptive Permeation Control," *Acc. Chem. Res.*, 19:57–63 no month available (1986).

Okahata et al., "The Electric Breakdown and Permeability Control of a Bilayer–Corked Capsule Membrane in an External Electric Field," *J. Am. Chem. Soc.*, 108:2863–2869 no month available (1986).

Okahata et al, "Permeability–Controllable Membranes. no month available 7. Electrochemical Responsive Gate Membranes of a Multibilayer Film Containing a Viologen Group as Redox Sites," *J. Phys. Chem.*, 92:4546–4551 (1988).

Okahata et al., "Permeability–Controllable Membranes. 8. Electrochemical Redox–Sensitive Gate Membranes of Polypeptide Films Having Ferrocene Groups in the Side Chains," *Macromolecules*, 22:308–315 no month available (1989).

Okahata et al., "Preparation of Bilayer–Intercalated Clay Films and Permeation Control Responding to Temperature, Electric Field, and Ambient pH Changes," *Langmuir*, 5:954–949 no month available (1989).

*Langmuir–Blodget Films*, ed. by Roberts, New York and Loundon: Plenum Press, pp. 53–58 no month available (1990).

*Primary Examiner*—Kathryn Gorgos
*Assistant Examiner*—John S. Starsiak, Jr.
*Attorney, Agent, or Firm*—Majestic, Parsons, Siebert & Hsue

[57] ABSTRACT

Devices are useful to capture or dispense target molecules and include an electric field-responsive valve unit. The valve unit includes an active control structure having at least one monomolecular layer and being up to about 10 nm thick. The active control structure is formed by a majority of molecular species with a dipolar moment greater than about 5 Debye, and operable in response to an electric field at a threshold value. A particularly preferred embodiment has the active control structure carried on a microporous membrane with pores in the nanometer range. Applications for inventive embodiments include drug delivery and target molecule capture during electrophoresis separations.

18 Claims, 7 Drawing Sheets

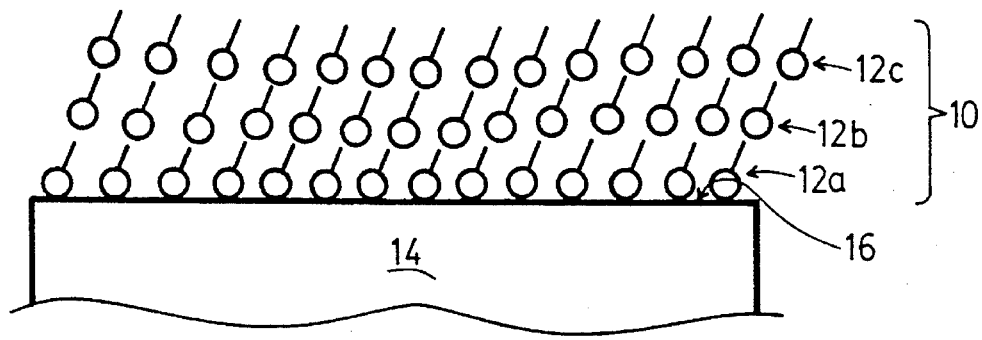
FIG._1.
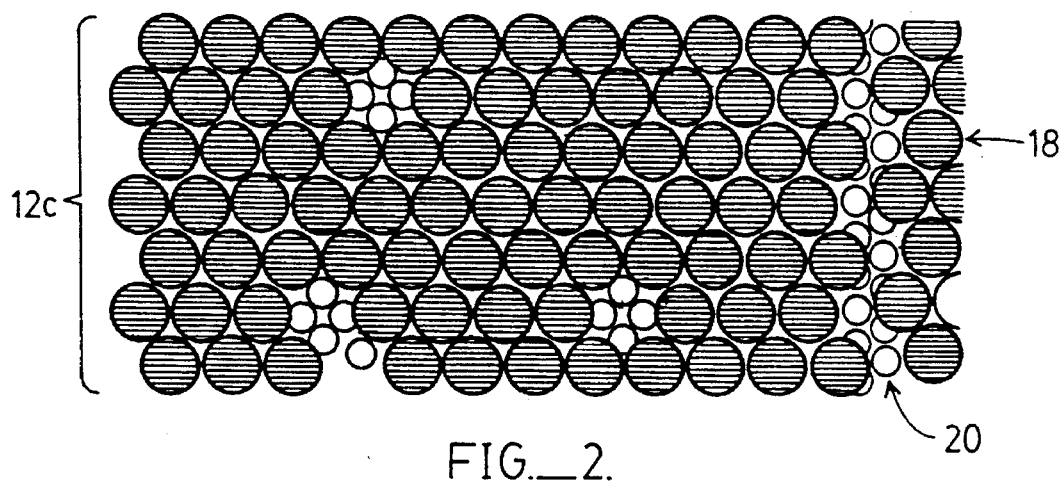
FIG._2.
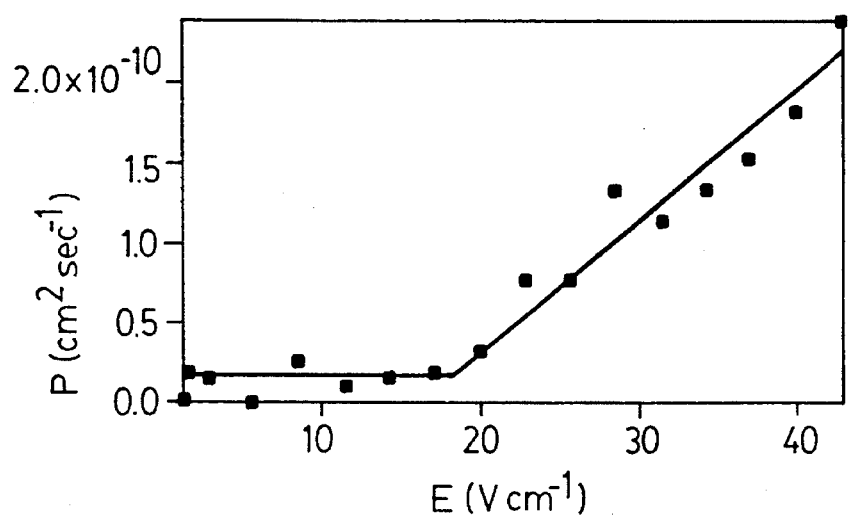
FIG._3.

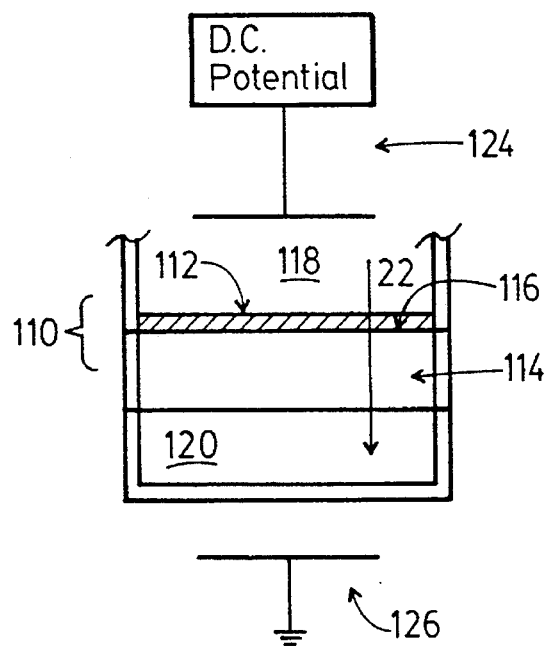
FIG._4A.
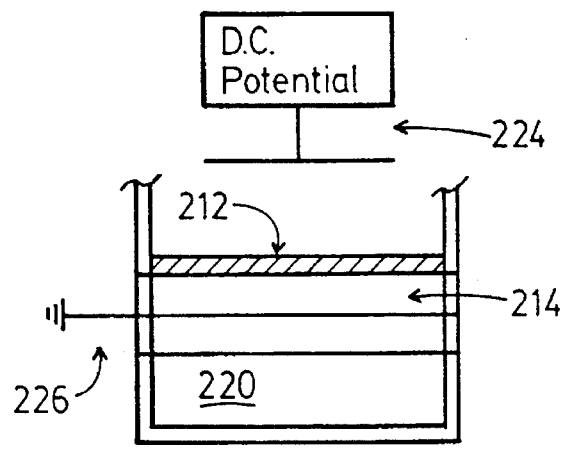
FIG._4B.
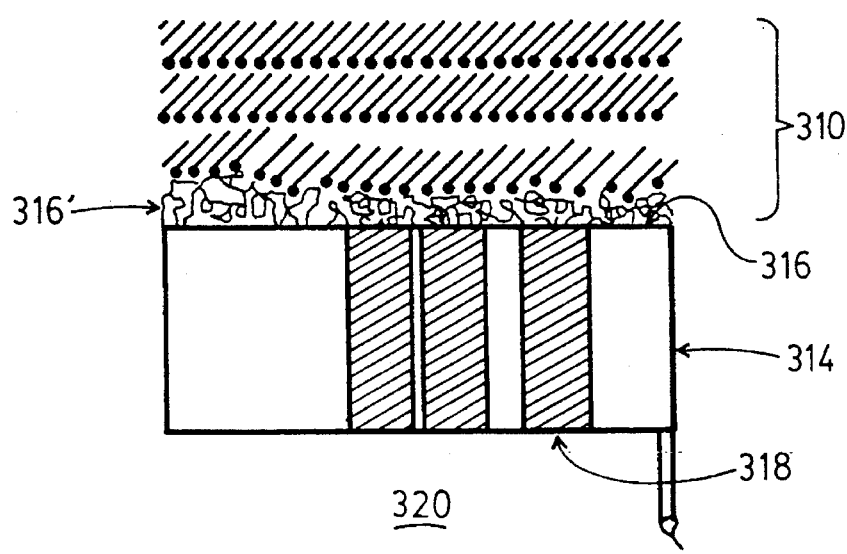
FIG._4C.

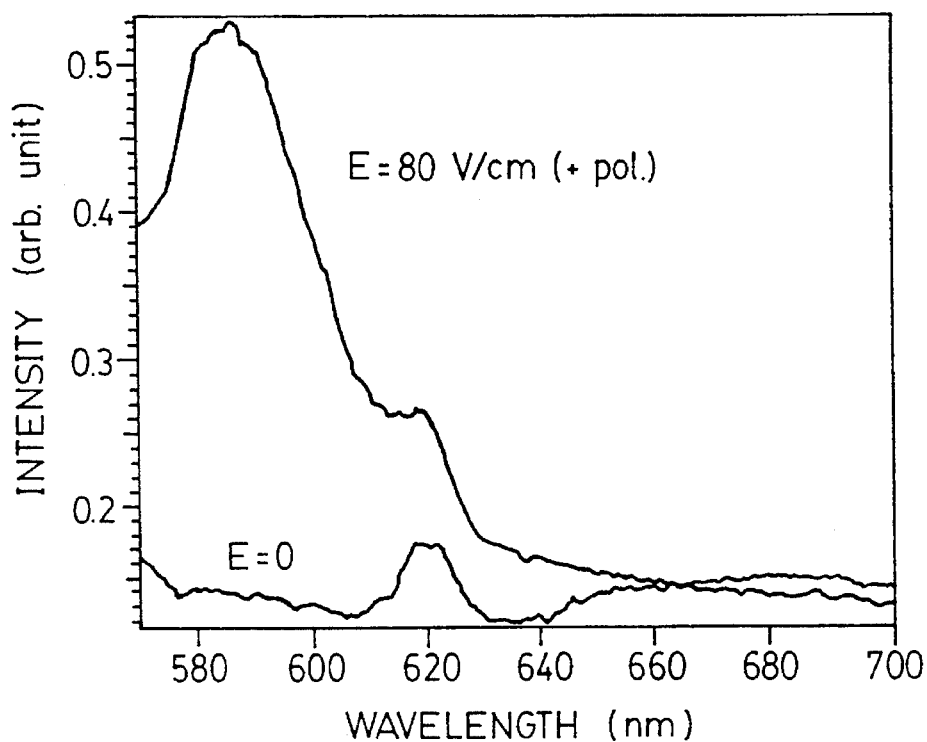
FIG._5.
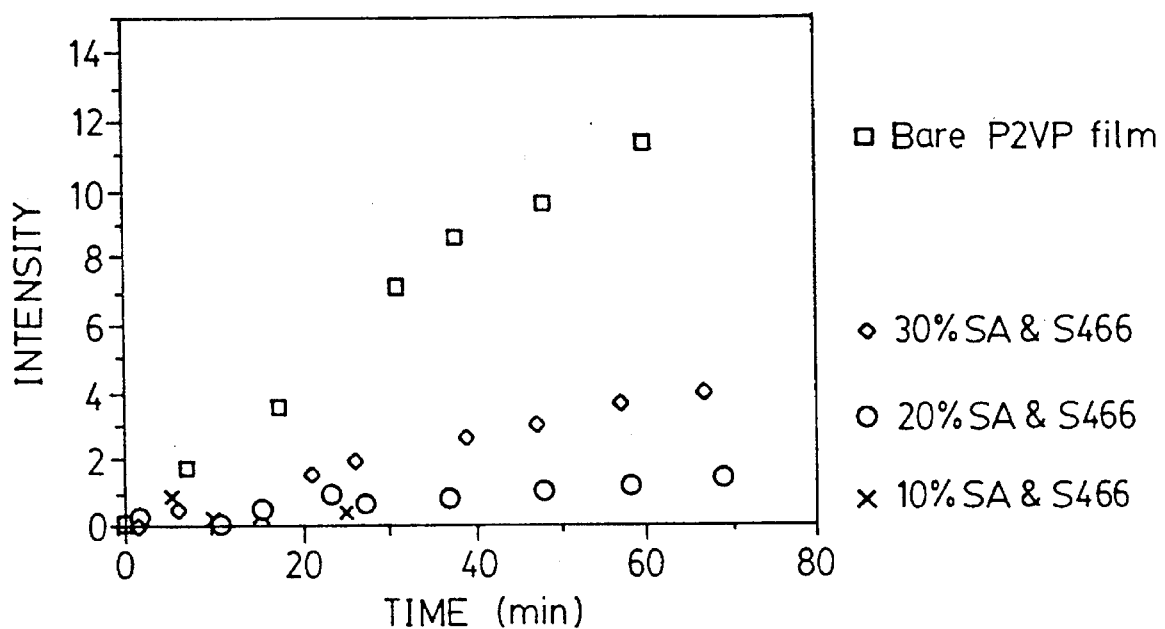
FIG._7.

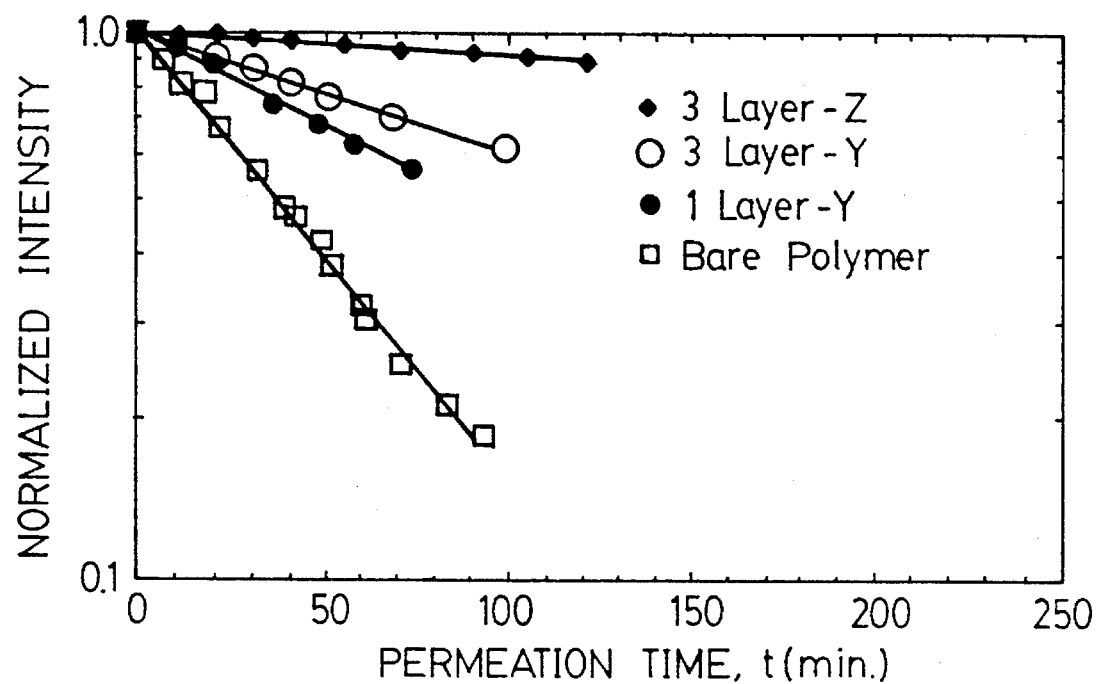
FIG._6A.
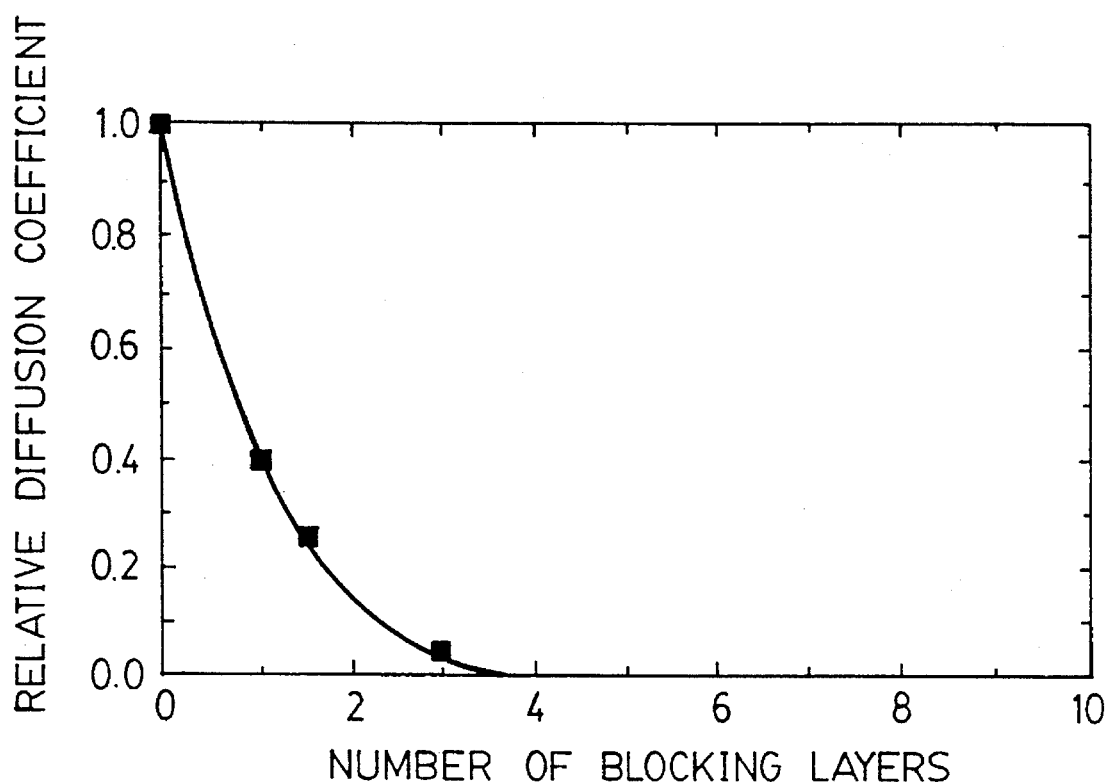
FIG._6B.

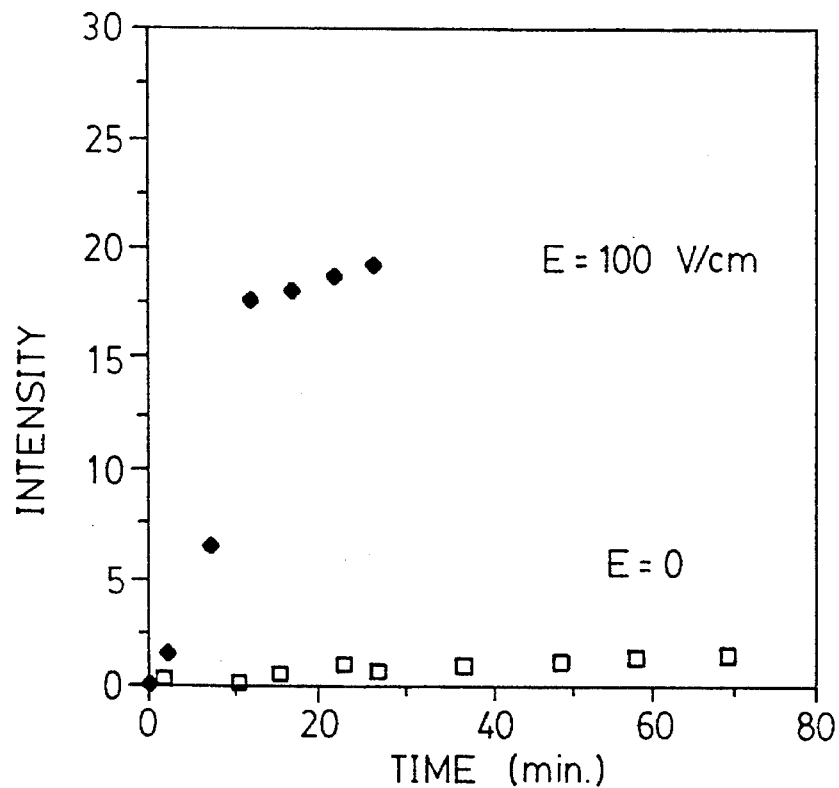
FIG._8A.
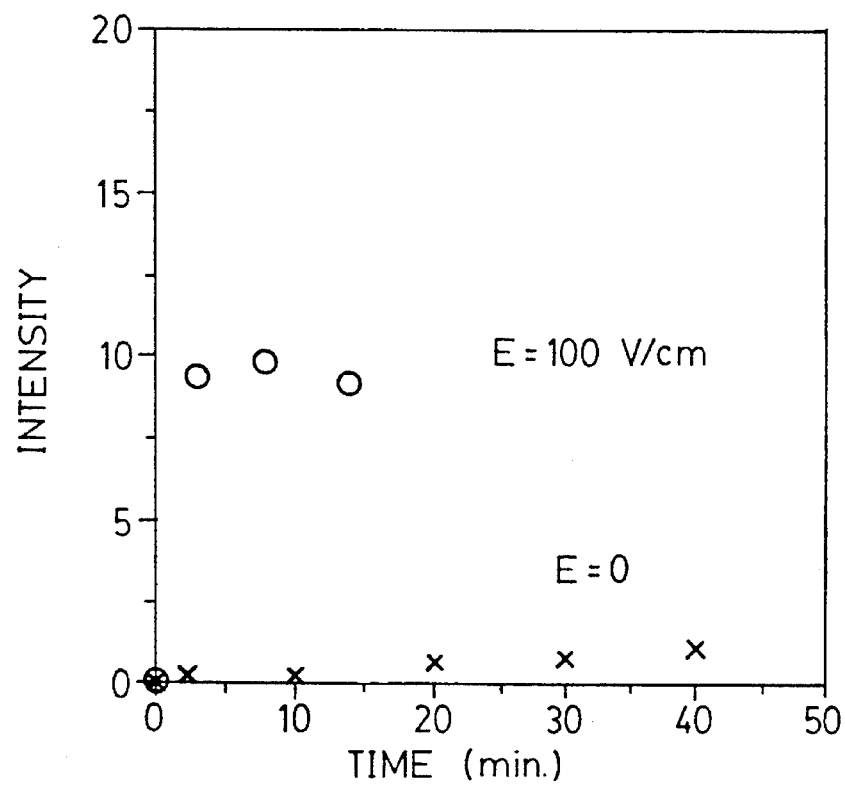
FIG._8B.

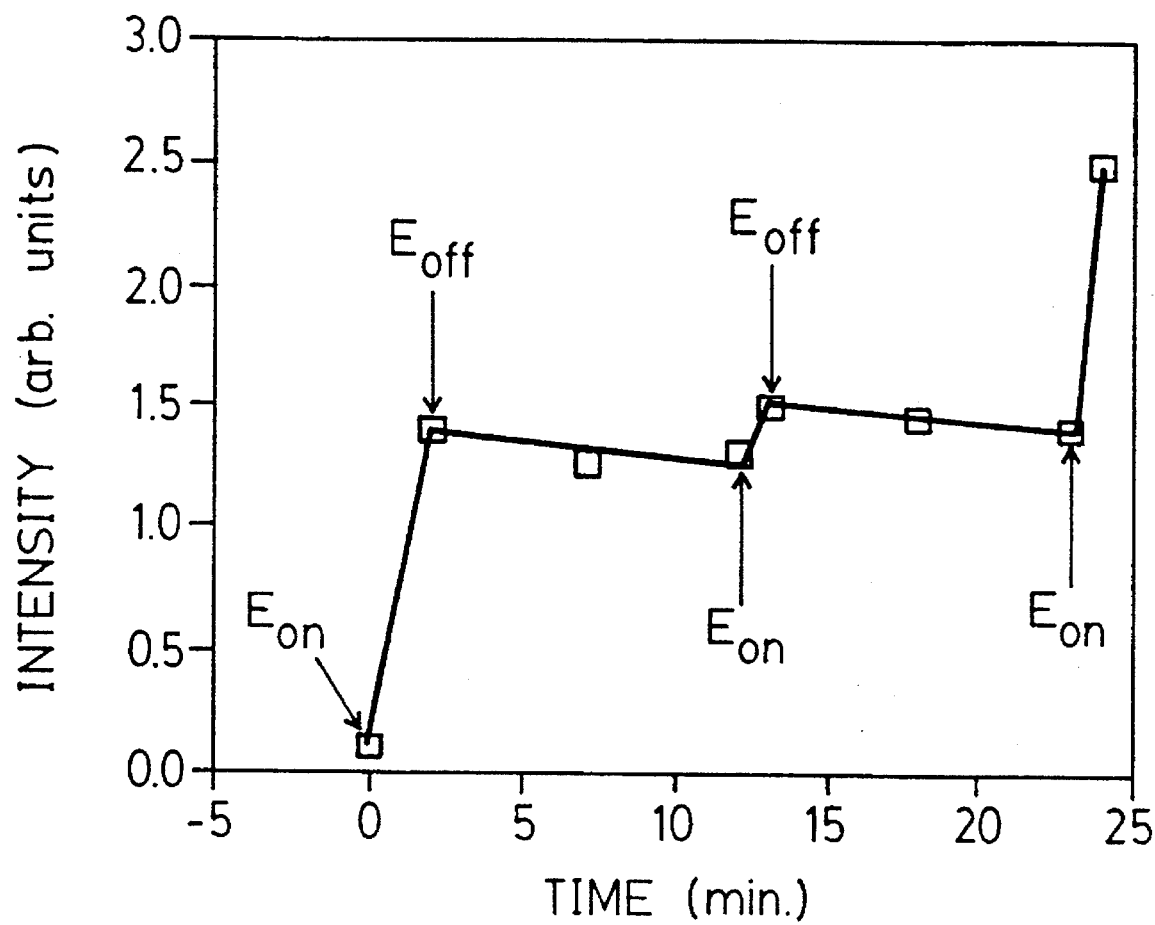
FIG._9.

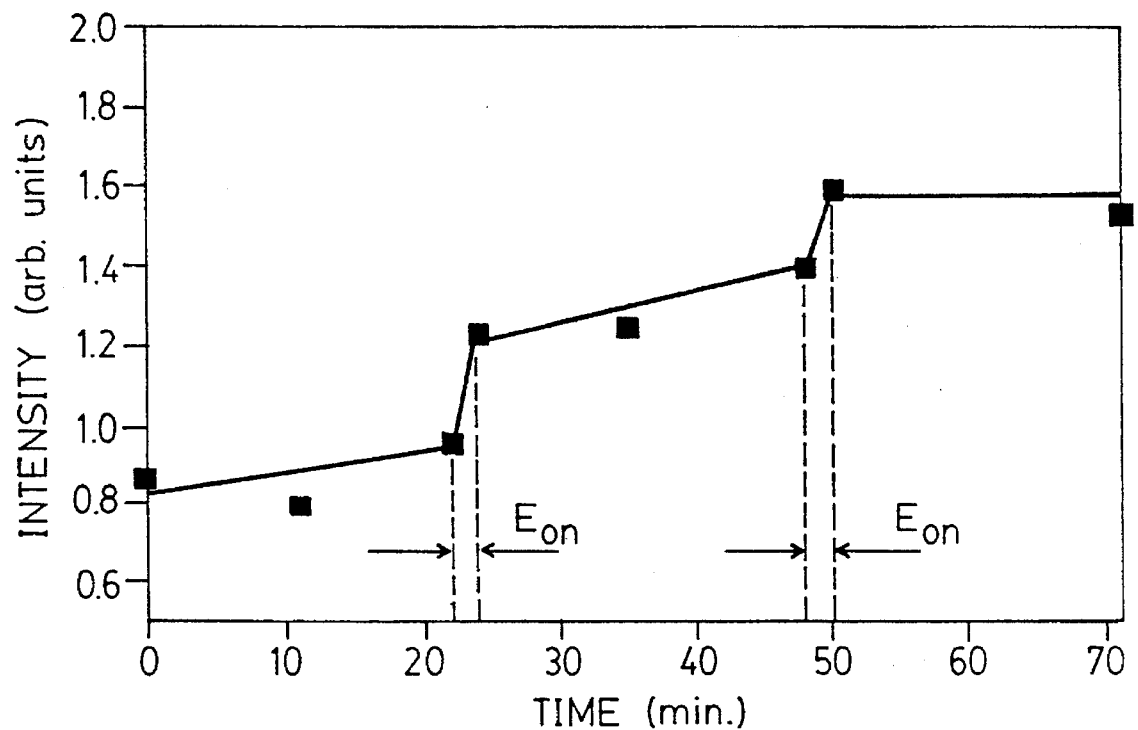
FIG._10A.
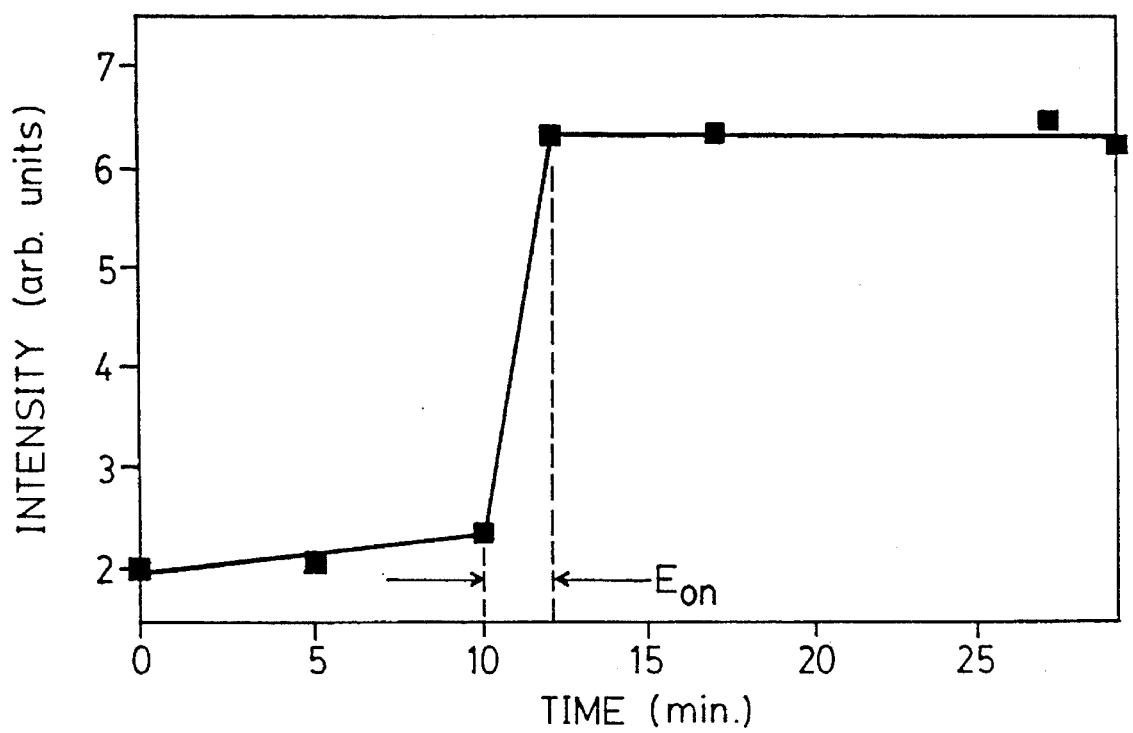
FIG._10B.

STRUCTURES WITH FIELD RESPONSIVE PERMEATION CONTROL

FIELD OF THE INVENTION

The present invention generally relates to structures that release or capture target molecules in a fluid by use of permeability control in response to an electric field, and more particularly relates to extremely sensitive and versatile assemblies useful in a variety of molecular sensing, separating, and switching applications by use of monomolecular layers whose permeation is controlled by an electric field.

BACKGROUND OF THE INVENTION

A good deal of research effort within the last decade has been conducted in correlating changes in permeability across bilayers where specific perturbations to the structure of the bilayers can be responsible for changes in permeability (from an "off" position to an "on," or "open," position). A leading researcher in the area has been Yoshio Okahata.

In the article "Lipid Bilayer-Corked Capsule Membranes, Reversible, Signal-Receptive Permeation Control," Acc. Chem. Res., 19, pp. 57–63 (1986), Okahata describes capsules formed of porous nylon. The nylon forms a capsule with an inner layer having pores on the order of 1–2 nm in diameter, while an outer layer has pores on the order of 100–300 nm in diameter. These pores are filled, or corked, with multilamellar bilayers such as $2C_{12}PO^-_4$. Okahata reported permeation enhancements under 60-V fields (60 kV $cm^{-1}$ since the capsule membrane is 1 µm thick). However, the corked capsules permitted slow permeation of NaCl, even in the absence of a field, at the rate of $5.5 \times 10^{-7}$ $cm^2$ $s^{-1}$, which slow "off" permeation rate increased slightly after a 3 minute charging duration to $5.7 \times 10^{-7}$ $cm^2$ $s^{-1}$.

Okahata et al., "The Electrical Breakdown and Permeability Control of a Bilayer-Corked Capsule Membrane in an External Electric Field," J. Am. Chem. Soc., 108, pp. 2863–2869 (1986), continues earlier studies with variations in the head groups for the bilayer-forming amphiphile.

Okahata and En-na, "Permeability-Controllable Membranes . . . Electrochemical Responsive Gate Membranes of a Multibilayer Film Containing a Viologen Group as Redox Sites," J. Phys. Chem., 92, pp. 4546–4551 (1988), report permeability rates of $3.0 \times 10^{-7}$ $cm^2$ $s^{-1}$ in an oxidized "off" form and permeability decreased by a factor of 5 ($6.3 \times 10^{-8}$ $cm^2$ $s^{-1}$) for a reduced "on" form.

Okahata and Takenouchi, "Permeability Controllable Membranes . . . Electrochemical Redox-Sensitive Gate Membranes of Polypeptide Films Having Ferrocene Groups in the Side Chains," Macromolecules, 22, pp. 308–315 (1989), describe synthetic polypeptide membranes that were cast on a platinum minigrid sheet. These films contained thiol groups that could be oxidized and reduced by electrochemical potentials. Permeation enhancement up to 6 times were reported, with permeability rates of the reduced form being about $5-12 \times 10^{-8}$ $cm^2$ $s^{-1}$.

Okahata and Shimizu, "Preparation of Bilayer-Intercalated Clay Films and Permeation Control Responding to Temperature, Electric Field, and Ambient pH Changes," Langmuir, 5, pp. 954–959 (1989), describe the preparation of a self-standing bilayer-intercalated clay film. These bilayer-intercalated clay films were prepared by admixing an aqueous colloidal solution of clay (montmorillonite) and an aqueous dispersion of ammonium amphiphiles. Precipitates were dried as powder and exchangeable cations in the interlayer of the clay were changed for cationic bilayer-forming amphiphiles. A self-standing film was cast on a polyester minigrid (50 µ/270 mesh, 70 µm thick). The film thickness was about 100 µm. X-ray analyses indicated film microstructure as being stacked clay layers, each separated by amphiphile forming bilayer structures in the clay interlayers. In the absence of electric fields, permeation was $1.2 \times 10^{-9}$ $cm^2$ $s^{-1}$ but with a DC applied voltage of 2.5 V (50 V/cm), permeability was enhanced.

These Okahata references all describe macroscopic assemblies utilizing bilayers, or multiples of bilayers, with the best "off" position permeability value being in the $10^{-9}$ $cm^2$ $s^{-1}$ range. However, composite structures with better "off" position permeability and highly controllable, reproducible permeability in fabricating structures are desirable.

Devices using amphoteric molecules or Langmuir-Blodgett film forming techniques have been recently described for various applications. Thus, U.S. Pat. No. 5,234,566, issued Aug. 10, 1993, inventors Osman et al., describes a biosensor having a lipid membrane. The membrane includes a gated ion channel. The membrane has a closely packed array of self-assembly amphiphilic molecules. In one form of the biosensor, the conductance of the ion channels is dependent on an electric field applied across the membrane. By "gated ion channel" is meant that the passage of ions therethrough is dependent on the presence of an analyte. The amphiphilic molecules are preferably cross-linked. Attachment of analyte to a receptor moiety attached or associated with the ion channel causes the receptor to change into a state where ions may pass through the ion channel.

Another recent device is described by U.S. Pat. No. 5,293,261, issued Mar. 8, 1994, inventors Shashidhar et al. This liquid crystal device has a Langmuir-Blodgett film of a liquid crystal polymer on a substrate between a pair of electrodes. The Langmuir-Blodgett film is said to undergo electric field-induced ferroelectric switching. The exemplary liquid crystal polymers of the film have poly(meth)acrylic, poly(meth)acrylate, and polysiloxane backbones, and the films are formed by dipping with five to fifty layers of LCP preferred.

A need exists for assemblies that are sensitive and selective for various molecular release or capture applications, but which are readily and reproducibly fabricated.

SUMMARY OF THE INVENTION

In one aspect of the present invention, an electric-field responsive assembly has an active control structure composed of at least one monomolecular layer. The one layer (and any additional monomolecular layers) is carried on a surface of a support that, without the active control structure, permits target molecules to diffuse therethrough. The active control structure is reversibly and reproducibly switchable between an "off" permeability value and an "on" permeability value for target molecules. "Off" permeabilities on the order of about $10^{-11}$ $cm^2$ $s^{-1}$ are achievable with inventive embodiments. Switching between off and on permeabilities is achieved by application of an electric field above a threshold value. Each monomolecular layer of the active control structure includes at least a majority of molecular species having a large ground state dipole moment. Each monomolecular layer has substantially all its molecules in a closely packed assemblage where the molecules are generally aligned along their long axes and packed in the monomolecular layer to be within about one short axis molecular diameter of each other.

Active control structures of the invention preferably are multilayers formed by a Langmuir-Blodgett technique and in X, Y, or Z configurations. Each molecular layer is substantially free of sites having a local permeability that is significantly higher than the average off permeability value. Particularly preferred active control structures have three more monomolecular layers, each of which is constituted by a majority of molecular species selected from aggregate-forming amphiphiles, particularly stilbene derivatives, thiacyanines, oxacyanines, merocyanines, and isocyanines.

One particularly preferred embodiment uses a microporous membrane, with pore diameters in the nanometer range. Such a nanoporous support carrying the active control structure can form a permeability controllable barrier, such as between two liquid cells or can be used as a membrane separation system for biomolecule separations.

In another aspect of the present invention, a molecular capturing or dispensing device comprises a field-responsive valve unit in fluid communication with a source of target molecules and an operable electrode assembly coupled to the valve unit for delivery of an electric field. The valve unit includes a very thin active control structure having at least one monomolecular layer of amphiphilic molecules. A majority of the amphiphilic molecules have a dipole moment greater than about 5 Debye. Each monomolecular layer of the active control structure has substantially all the molecules closely packed with respect to a short axis while the molecules are generally aligned with respect to long axes.

BRIEF DESCRIPTION OF THE DRAWINGS

FIG. 1 illustrates in greatly enlarged cross-section an essential component of the invention;

FIG. 2 is a plane view of the FIG. 1 component;

FIG. 3 graphically illustrates a property for an embodiment of the invention;

FIG. 4 in panels A–C schematically illustrate several embodiments of the invention with differently configured components; and FIG. 5 shows the difference in fluorescence spectra of a rhodamine B derivative probe with and without the application of an electric field in an embodiment of the invention. With the neutral rhodamine B derivative, the rate of permeation is lower than with a probe such as fluorescein, since it is zwitterionic and electromigration is not a factor.

FIG. 6 in panels A and B shows the initial portion of the kinetic curve for permeation into a P2VP film covered with various types of overlayers and also shows the apparent diffusion coefficient as a function of the number of Z-type layers deposited.

FIG. 7 shows the comparison of zero-field permeation rates for various film compositions.

FIG. 8 in panels A and B illustrates the permeation control by application of an electric field: (A) permeation results both with and without applied field for a film which is 1:4 stearic acid ("SA") and a first amphiphile (I); (B) permeation results both with and without applied field for a film which is 1:9 stearic acid and a second amphiphile (II).

FIG. 9 shows the response of permeability to repeated 30-second electric field cycling in a 1:4 SA:II trilayer.

FIG. 10 illustrates the response of preloaded P2VP films to reverse polarity field, where panel A plots small pulse duration application over two cycles, and panel B plots larger pulse duration where all material loaded into the film is removed.

DETAILED DESCRIPTION OF THE PREFERRED EMBODIMENTS

Applications for the inventive embodiments that will be more fully described hereinafter include drug delivery devices and components for target molecule capture in preparative gas or liquid chromatography systems, including capillary zone electrophoretic apparatus.

For example, dispensing mechanisms for drug delivery are being developed that incorporate electrodes for controlled drug delivery. U.S. Pat. No. 5,290,240, issued Mar. 1, 1994, inventor Horres, describes aspects of this evolving field, and more particularly describes an infusion pump assembly using electrochemistry to selectively control the delivery rate of a dispensing fluid from a dispensing reservoir by selectively controlling the flow rate of a driving fluid from a driving reservoir to a receiving reservoir. U.S. Pat. No. 5,288,289, issued Feb. 22, 1994, inventors Haak et al., describe another drug delivery apparatus said to be useful for treating a tumor with antitumor sensitizing agents, biological modifiers, antibiotics, or the like. This patent characterizes the emerging technology as "iontophoresis technology," which uses an electric potential or current, in transdermal drug delivery. Electrode structures for transdermal drug delivery in iontophoretic transport are also described by U.S. Pat. No. 5,284,471, issued Feb. 8, 1994, inventor Sage. While the present invention does not utilize an iontophoresis mechanism, the just noted patents illustrate drug delivery applications and electrode structures of interest for the invention.

Another application with which embodiments of the invention are useful is in chromatography or electrophoresis. Electrophoresis is a well-known technique for the separation of charged species by utilizing their differences in rate of migration under the influence of an electrical field. Free electrophoresis has been largely supplanted by various forms of zone electrophoresis in which an aqueous protein solution is immobilized in a solid matrix that provides mechanical rigidity and reduces convection and vibration disturbances.

Capillary zone electrophoresis ("CZE") in small bore capillaries is proving useful as an efficient method for the separation of certain solutes. A variety of detectors have been developed for CZE. For example, U.S. Pat. No. 5,298,139, issued Mar. 29, 1994, inventors Huang & Zare, describes an end-column conductivity detector. Other CZE systems are noted in, for example, U.S. Pat. No. 5,180,479, issued Jan. 19, 1993, inventor Rose, while U.S. Pat. No. 5,114,768, issued May 19, 1992, and U.S. Pat. No. 4,931,328, issued Jun. 5, 1990, inventor Swedberg, discuss approaches in CZE for separating solutes, including macromolecules. Inventive embodiments can be used downstream of CZE detectors to selectively capture certain solutes as target molecules, which have been detected upstream.

Embodiments of the invention include an active control structure formed of controlled amphiphilic assemblies selectively perturbed by an electric field. The active control structure may be carried on a surface of a support. The supports would normally permit target molecules to diffuse therethrough in the absence of the active control structures, and provide structural integrity for the active control structures. The combination of an active control structure in accordance with the invention having sufficient structural integrity for fabrication and use in assemblies, such as for molecular capturing and releasing applications, constitutes an essential element of all the inventive embodiments, and is sometimes referred to as a "valve unit."

Such a valve unit can be variously multiplied, depending upon the particular applications desired. For example, the number of supports (with one or more surfaces carrying active control structures) can be multiplied so that the valve units are in some definite, selected spatial relation one to another. In such multiple valve unit embodiments, the particular materials used in forming the different supports can themselves be different, and the molecular species constituting the various active control structures can likewise differ. This ability to multiply valve units provides considerable flexibility in controlling the path taken by target molecules traveling from a fluid source and can form a biomembrane "superlattice."

Suitable supports of the invention permit facile, diffusive transport of target molecules in a fluid. By "fluid" is meant to include gas, liquid, and vapor phases. The target molecules themselves may vary from small molecules to large, depending upon the desired applications. As already noted, drug delivery apparatus applications can use as "target molecules" growth factors, antitumor sensitizing agents, biological modifiers, antibiotics, or the like. Electrophoresis and chromatography systems applications will also pertain to "target molecule" captures over a considerable size range. Rhodamine B, which is used as one illustrative target molecule in FIG. 5 in illustrating aspects of the invention, has a molecular weight of 479 and a structure of 3 fused rings, the central ring being further substituted by a carboxyphenyl.

The fluid serving as a transport medium for the target molecules is typically a liquid solvent for the target molecules (preferably water), but the target molecules themselves may be in sufficient quantity as to comprise the entire fluid flow.

Suitable supports may take a wide variety of sizes, shapes, and be formed of a great number of materials. Supports will typically have thicknesses in the range of about $10^3$ nm or larger. Among the many suitable materials that may serve as supports are gel matrices, such as agarose and agarose derivatives, acrylic polymers, such as polyacrylamide, and vinyl polymers, such as poly(vinyl)pyridine. Suitable supports can swell in the fluid used as the flow media if desired. In this instance the swelling is normally accomplished directly in the Langmuir trough, since the substrate will be held under the water surface (that is, in the subphase) during the compression part of the preparation. Normally, about a monolayer of water is carried with the monolayer forming the active control structure during transfer. Thus materials such as hydrogels can be used. Supports can be formed of polymeric networks, such as a cross-linked polymeric network prepared by free radical bulk copolymerization by admixing hydrophobic monomer, weakly basic monomer, and cross-linking reagent in the desired proportions. Polymerization may be initiated by photoinitiation, irradiation, or the addition of a polymerization inhibitor. We have used poly(2-vinyl)pyridine ("P2VP") to illustrate aspects, or some embodiments, of the invention.

Supports, of course, can be composites of materials so long as they provide sufficient structural integrity so as to position and retain the active control structure as desired in the assembly.

No particular surface pretreatment of the support is required, although the type of surface chemistry influences what film configuration will be selected for the active control structure. For example, when the surface is hydrophilic, then typically one prefers a hydrophilic "head group down" orientation (that is, a Y- or Z- configuration). Alternatively, if the surface is naturally hydrophobic, then one would typically perform an "X-configuration" deposition where the hydrophobic tails are adjacent to the surface. One can, of course, convert the surface from hydrophilic to hydrophobic (and vice-a-versa) via appropriate chemical pretreatments known to the art. Chemical pretreatments can often involve uses of organic silanes, some of which are discussed for modifying inorganic oxide substrates in U.S. Pat. No. 5,017,540, issued May 21, 1991, inventors Sandoval and Pesek and some other surface treatments for constructing Langmuir-Blodgett switching devices (with ferroelectric liquid crystal polymer films) are discussed in U.S. Pat. No. 5,283,261, issued Mar. 8, 1994, inventors Shashidhar et al.

Where supports have a substantial fluid capacity (e.g. hydrogels), then they can also function as the fluid reservoir that is spaced from the fluid source of target molecules and has the active control layer interposed between the fluid source and the reservoir. Particularly preferred supports are nanoporous materials, such as nuclear track-etched membranes (e.g. Nucleopore polycarbonate membranes).

The active control structure of the invention will be on the order of between about 1 nm to about 10 nm thick with at least one monomolecular layer, and more typically will have a plurality of layers (preferably 3 to about 10) each of which is a single molecule thick. With reference to FIG. 6, panel B, one sees that at about 3 monolayers for the system represented by the figure data, there was achieved permeability blocking of about 2 times or better. The system whose data is represented by panel 6B was an admixture of 4,4-(dihexadecylaminostyryl)-N-methylpyridinium iodide (sometimes referred to as "D3883" or "C16" or "amphiphile (II)") and 10% stearic acid with "Z" configuration LB monolayers.

Each layer is controlled as to the desired properties pertaining to permeability for the target molecules. Thus, each layer is composed of amphiphilic molecules, at least a majority of which have a large ground state, permanent dipole moment (typically greater than about 5 Debye). These amphiphilic molecules typically have delocalized $\pi$ electrons so the dipole is extended over the $\pi$ electron network. The generic structures of some suitable aggregate-forming amphiphiles for preparing active control structures of the inventions are illustrated in Table 1.

TABLE 1

| Amphiphilic Type | Structure |
|---|---|
| stilbazolium hemicyanines | 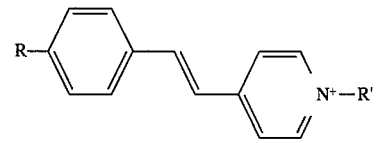 |
| R = $CH_3(CH_2)_m{}^{-1}$<br>R' = $(CH_2)_n{}^{-1}CO_2H$<br>stilbene derivatives | 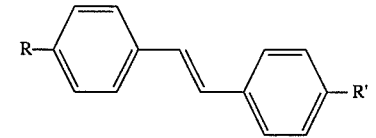 |

TABLE 1-continued

| Amphiphilic Type | Structure |
|---|---|
| thiacyanines | 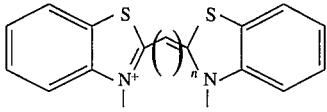 |
| oxacyanines | 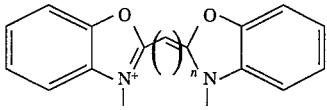 |
| merocyanines | 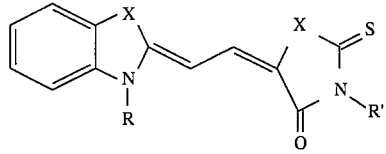 |
| isocyanines | 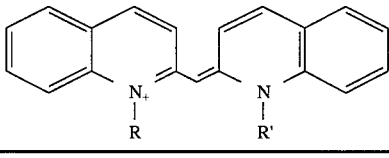 |

The R and R' groups of the Table 1 compounds are normally alkyl chains with from about 1–30 carbons, more preferably about 8–20 carbons. Although suitable chromophores having a large ground state dipole moment and useful in forming active control structures of the invention, such as the Table 1 compounds, are probably more rod-like in nature, we will use the more typical "head" and "tail" terminology. FIG. 1, for example, uses circles to illustrate head groups and radiating lines to suggest the tail groups.

These Table 1 aggregate-forming amphiphiles are relatively robust. Some have head groups that are zwitterionic. It is believed that the attractive forces provided by the interaction of the conjugated π systems enhance those provided by the zwitterionic head group, and thus assist in providing stability for the aggregate structure. However, ionic (e.g. cationic) head groups, such as R—$N^+$—φ, are also useful.

The active control structure preferably includes a majority of such molecular species with a large ground state dipole moment (e.g. the Table 1 compounds), and more preferably is on the order of about 70 mole percent or more, most preferably from about 70% to about 90% (mole percent). However, admixtures of amphiphiles are preferred in forming the monomolecular layers. This is because the large dipole moment molecular species tends to form domains when aggregating. Since interstices, or pores, might occur between these domains, we prefer to mix in minor amounts of simple amphiphilic molecules. Thus, for example, FIG. 2 illustrates the large ground state dipolar moment species (shown as larger diameter, dark shaded circles) with minor amounts of simple amphiphilic molecules as space filing molecules (the smaller diameter circles).

The simple amphiphilic molecules used in forming the admixtures for the active control structure compositions are also dipolar, but are believed not to respond significantly to an electric field or at least respond less than those molecules with dipole moments larger than about 5 Debye. The simpler species have alkyl chains forming hydrophobic tails, but typically have simple polar head groups (such as carboxyl, alcohol, quaternary amines, and sulfonates). The alkylene units forming the fatty acid tails are preferably about 12 carbons or longer (up to about 30 carbons). The fatty acid chains may contain some unsaturation, but little or no branching. For example, these simple amphiphilic components may be composed of such species as dodecanoic acid, $CH_3(CH_2)_{10}CO_2H$; tridecanoic acid, $CH_3(CH_2)_{11}CO_2H$; and tetradecanoic acid, $CH_3(CH_2)_{12}CO_2H$. To further illustrate, simple amphiphilic compounds may be: pentadecanoic, $CH_3(CH_2)_nCO_2H$, where n=13, or hexadecanoic, where n=14, or heptadecanoic, where n=15, or octadecanoic, where n=16, or nonadecanoic, where n=17, or eicosanoic, where n=18, or hemeicosanoic, where n=19, or docosanoic, $CH_3(CH_2)_nCO_2H$, where n=20, and so forth. In a similar manner $C_{12}$–$C_{30}$ alcohols, such as those corresponding to the just illustrated carboxylic acids, are useful. Among the quaternary amines that may be used as the simpler species are those with single, double, or triple chains. If one chooses a simpler species with a sulfonate head group, then substantially any of the conventional cations as counterion may be present, including, for example, organic cations such as tetramethyl ammonium.

Although about 70%–90% of the larger ground state dipole moment amphiphiles are preferred, the relative molar proportions of admixtures will vary, depending upon the particular surface chemistry of the support chosen. With reference to FIG. 7, one sees data showing that admixtures of 10 to 20% stearic acid with N-(3-sulfopropyl)-4-(p-dioctylaminostyryl)pyridinium (sometimes termed "S466") or amphiphile (I) were better at blocking permeability than an admixture including 30% stearic acid. Also ascertained for the system from which the FIG. 7 data was taken (but not illustrated therein), was that a monolayer formed from pure amphiphile (I) was less effective in blocking permeation than the 30% stearic acid admixture.

Each monolayer of the active control structure is composed of dipolar molecules that are substantially aligned along their long axes. The molecules of the monolayers must be closely packed, preferably so as to be within about a molecular diameter of each other (with respect to the short axis of the molecules). Such close packing is preferably achieved by means of a Langmuir-Blodgett technique, which typically involves depositing a solution of amphoteric molecular species in volatile solvent onto the surface of a highly purified water. The solvent is evaporated, which leaves an ultrathin film of the amphoteric molecules on the water surface. This film is compressed with a partially submerged, moveable dam while holding the film at a constant degree of compression or surface tension by means of a computer-controlled film balance. The support may be dipped vertically or horizontally into and out of the film-water interface, thereby coating the support with the closely packed monomolecular layer. The characteristics and preparation techniques of Langmuir-Blodgett films are described, for example, in *Langmuir-Blodgett Films*, Gareth Roberts, ed., (Plenum Press, New York, N.Y. 1990) and *An Introduction to Ultrathin Organic Films from Langmuir-Blodgett to Self-Assembly*, Ulman (Academic Press, Inc., San Diego, Calif. 1991).

Unlike self-assembled bilayers or multilamellar structures known to the art and used, for example, by the earlier mentioned Okahata references, Langmuir-Blodgett films are not only more closely packed, but the monomolecular layers can be formed with multiple layers in different relationships (from one layer to another) than occur in self-assembled bilayers. In self-assembled bilayers, the hydrophobic tails assemble end-to-end with the hydrophilic head groups outwardly positioned. That is, multiple bilayers will stack in a head-to-head orientation. However, with Langmuir-Blodgett films the head groups of one layer may be aligned with respect to the tail groups of the next adjacent underlayer (that is, in a "Z" configuration). Indeed, the "Z" configuration for active control structures of the invention are particularly preferred, as is suggested by panel A of FIG. 6, where a three layer "Z" configuration active control structure (composed of amphiphile (II) and 10% stearic acid) gave the best performance of decreased permeation with respect to a three layer "Y" configuration and a one layer "Y" configuration (and all with respect to bare, or uncoated, P2VP film as support).

The monomolecular layers constituting the active control structure are thus artificial molecular assemblies with selectable spatial and orientational order, which act collectively in response to an electric field at or above a threshold value. Thus, with reference to panels A and B of FIG. 8, the active control structure is shown to be highly impermeable in the absence of electric field but also shown to be highly permeable in the presence of sufficient electric field. The active control structures from which the FIG. 8 data was taken were "Z" type trilayers. With reference to FIG. 9, reversibility of permeability is illustrated to repeated electric field cycling the active control structure was in a "Z" configuration. With reference to FIG. 10, panel A shows that probe (here fluorescein) that was preloaded into the P2VP film was able to release the probe in increments as a function of applied electric field, while panel B shows that substantially all the preloaded probe could be released at once upon application of the appropriate electric field. Thus, the FIG. 10 data illustrates applicability of the inventive embodiments as dispensing devices, as well as for capturing target molecules.

Turning to FIG. 1, an active control structure embodiment of this invention is illustrated in greatly enlarged cross-section where a valve unit 10 is composed of monomolecular layer 12a, monomolecular layer 12b, and monomolecular layer 12c. These layers 12a–c form the active control structure, which is illustrated in a "Z" configuration. The active control structure 12 is carried by support 14 along surface 16. Microscopic structural irregularities of the surface 16 tend to be taken up by the first layer 12a, and is a reason that we prefer using more than one monomolecular layer. As earlier noted, most preferably we prefer three monomolecular layers (and up to about 10). Too many layers can lead to slow transport of target molecules across the active control layer. As is illustrated by FIG. 1, the dipolar molecules of each monolayer are generally aligned along their long axes (long axes typically have a length of about a nanometer, $1.0 \times 10^{-9}$ m).

Turning to FIG. 2, a plane view of the uppermost layer 12c is shown where molecules 18 of the large moment dipole molecular species are closely packed to within about one molecular diameter of each other (with respect to the short axis, typically within about $0.5 \times 10^{-9}$ m). FIG. 2 also illustrates the admixture of molecular species in the monomolecular layer 12c. Molecular species 20 are the simple amphiphilic molecules or molecular species that do not respond significantly to the electric field (that is, have a relatively small ground state dipole moment). These "small dipole moment" molecular species function somewhat like mortar where the large dipole moment molecular species are something like bricks. That is, the small dipole moment molecular species can be viewed as a fatty acid matrix that fills in or prevents interstices occurring between aggregated domains of molecules 18. As a consequence, each monomolecular layer is substantially free of sites having a local permeability that is significantly higher than the average "off permeability value," as will be described more fully hereinafter.

The active control structures 12 of a valve unit 10 of the invention have an average "off" permeability value for target molecules that is extremely small in the absence of an electric field or in the presence of an electric field below a threshold value. This is illustrated by FIG. 3, where an inventive embodiment had an average off permeability value of about $2.0 \times 10^{-11}$ cm$^2$ s$^{-1}$ at applied electric fields from 0 to about 18 V/cm; however, at about 18 V/cm, the active control structure became rapidly, increasingly permeable to target molecules. The embodiment from which the FIG. 3 data was compiled was a trilayer active control structure in a "Y" configuration, with each monolayer of the three layers formed from amphiphile (I) and 10% stearic acid. The support was poly(styrene sulfonate) a top a nanoporous polycarbonate membrane. The electric field threshold value for this particular system was 18 V/cm.

The active control structure has an "on permeability value" (or range of values) enhanced with respect to the off permeability value. The particular threshold value for any particular active control structure 12 will vary depending upon differences in materials utilized and differences in dimensions. The amount of enhancement will be proportional to the applied field.

Typical threshold values for the applied field used to control permeability will be in the range of about 1–50 V/cm (dc of either polarity), although the applied electric field used for the FIG. 5 was 80 V/cm and for the FIG. 8 data was 100 V/cm. Miniaturized assemblies of the invention (such as may be desired for implantable drug delivery devices) will require proportionately small voltages. We have achieved permeabilities enhanced about 20 times with respect to average off permeability values, and greater enhancements should be possible, if desired, by using apparatuses with greater applied fields.

Electric fields can be applied for permeability control to valve units of the invention by electrodes external to the electric-field responsive assemblies of the invention or with one or both electrodes incorporated into the inventive assemblies. Thus, an electrode assembly will be operably coupled to the valve unit (or a plurality of valve units) for delivery of an electric field at or above the selected threshold value. The choice of electrode materials and type of power supply (e.g. batteries or the like) will be dictated in large part by the particular, desired application. A variety of suitable electrode structures are known to the art. Among electrode structure forming techniques useful in preparing devices of this invention are photoresist techniques. By employing modern photolithographic techniques for the preparation of the electrodes, it is possible to construct electrodes having a thickness as low as a few nm. Such photolithographic techniques are described and reviwed in Thompson et al., *Introduction to Microlithography*, ACS Symposium Series, Washington, D.C. (1983).

Turning to FIG. 4, panels A–C illustrate several embodiments of the invention with differently configured components.

A simple embodiment is shown by panel 4A where valve unit 110 is composed of active control structure 112 carried by porous support 114 on a substantially planar surface 116. A fluid source 118 has target molecules (not illustrated) therein. A fluid reservoir 120 is spaced from the fluid source.

As earlier noted, the support and the fluid reservoir can be a single component, not here illustrated but readily understood. Arrow 122 indicates a fluid passageway by which target molecules may flow between source 118 and reservoir 120 with the valve unit 110 interposed in the passageway. A pair of electrodes 124 and 126 may be arrayed so as to permit the application of an electric field across valve unit 110.

Panel 4B illustrates another embodiment configuration where the fluid source 218 and the fluid reservoir 220 form a passageway (arrow 222), and the active control structure 212 is carried by surface 216 of support 214; however, electrode 226 is now part of, or assembled with, structure 214.

Turning to panel 4C, another electric-field responsive assembly embodiment is illustrated, with valve unit 310. Valve unit 310 is carried on surface 316 of support 314. Support 314 includes pores 318 opening to fluid reservoir 320 (shown partially broken away).

Support 314 is formed of a nanoporous material having pore diameters on the order of between about 100 Å to about 1000 Å, preferably about 150 Å. Because surface 316 would not support the active control structures 312 in a sustained fashion (that is, the active layers would not remain intact, but would tend to collapse into the pore openings), a pore bridging material 316' is added along the surface 316 so as to support the active control structures 312. A stable composite system is thus formed. Suitable bridging materials for forming the layer 316' include polymeric networks, such as from sodium polystyrene sulfonates (molecular weights 70,000 to about 500,000), which can bind to moieties used in the active control structures (e.g. covalent binding) and/or be impregnated along the surface 316 (e.g. adsorption).

As earlier noted, embodiments of this invention may comprise a plurality of the different components selected in forming field-responsive valve units with operable coupled electrode assemblies in discrete arrays, and where the valve units may be bidirectional.

Aspects of the invention will now be illustrated by reference to the following examples, which are intended to illustrate, but not limit, the invention.

EXAMPLE 1

Pure and mixed monolayers and multilayers of two different, amphiphiles, which were hemicyanine dyes, N-(3-sulfopropyl)-4-(p-dioctylaminostyryl)pyridinium (I) and 4-(4-dihexadecylaminostyryl)-N-methyl pyridinium iodine (II) having the structures

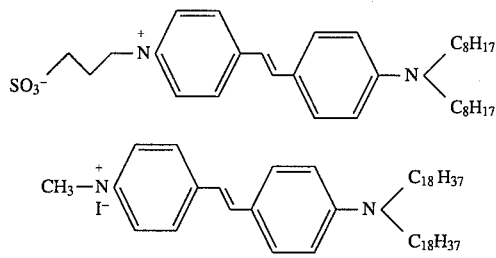

were prepared by alternate deposition of P2VP (representing a fluid reservoir of the invention) and the amphiphile on a quartz substrate, with or without integral semi-transparent electrodes. The P2VP film was coated on a quartz (fused silica) support, or substrates, by vertical dipping. The solution was prepared by dissolving P2VP in chlorobenzene with the aid of sonication. The dipping speed was 6 mm/min. After emersion the film was then annealed in vacuum at 120°–140° C. for two hours. The thickness of such a film was 500 Å to 1000 Å as revealed by profilometer measurements. The P2VP substrate was preswollen in water for at least one day before transfer of the active control structure onto the P2VP surface. The monolayer and trilayer structures of the amphiphile were fabricated using the Langmuir-Blodgett technique.

A 1 mM solution of the active control amphiphile, with or without addition of filler molecules, in chloroform was applied to the air-water interface, using high purity solvents and a deionized water subphase (18 MΩ-cm). After sufficient time to allow the chloroform to evaporate and any aggregation caused by self assembly to reach steady state (~60 minutes), a surface barrier was moved at a constant rate (1–10 mm/min) to compress the film into a single molecular layer. Transfer of this monomolecular layer onto the P2VP coated, fused-silica substrate was accomplished at constant surface pressure (20–40 mN/m) at an emersion rate of 10–20 mm/min.

When integral semi-transparent electrodes were desired, the following procedure was used. The preparation of a conductive slide normally includes four major steps: (a) derivatization of a surface such as silica with a heterobifunctional linker, (b) deposition of a gold film (or platinum or other suitable conducting layers that can be fabricated as thin films by means such as thermal evaporative sputtering, typically optically transparent and with a thickness of about 150 Å), (c) derivatization of the gold surface with the heterobifunctional reagent, and (d) deposition of oxide overlayer.

A new substrate is cleaned, first by immersion in hot concentrated sulfuric acid followed by rinsing with copious amount of deionized water. This process is repeated and then the slide is rinsed with copious amounts of 18.2 MΩ-cm water. The slide is then rinsed with acetone and dried in an oven at 150° C. for 20 minutes. Mercaptopropyl trimethoxysilane is added to a chloroform solution in the amount of 1% by volume. The solution is introduced into a three-neck round bottom flask connected with a reflux tube. The slide is placed in a slide holder and completely immersed in the chloroform. This system is then subjected to a mild reflux for 3.5 hours. After refluxing, the slide is washed with chloroform and allowed to dry in air. The chloroform solution is then sealed in the glassware and saved for later use.

The deposition of 100 Å of gold was performed in a commercial vacuum evaporator from an alumina crucible. The deposition speed was about 1 Å/s. The gold was 99.9% pure. The oxide substrate covered by the newly deposited gold film was then put back into the above-mentioned chloroform solution(with the linking agent). The slide was left in this solution overnight at ambient temperature. Then the slide was taken out of the solution, washed with chloroform and then dried in air at room temperature.

EXAMPLE 2

Nanoporous materials were used as a support in this embodiment. Bare membranes with pore diameters as small as 150 Å do not support LB monolayers or multilayers in a sustained fashion, i.e. in such a manner that the active layer remains intact. In order to build a sustained layer of LB films spanning the nanopores, we have used sodium polystyrene sulfonates (MW 70,000 or 500,000) PSS⁻Na⁺) to serve as a bridge above the nanopores and to support subsequent LB films transferred onto the surface at a surface pressure of 30–40 mN/m. In the case of cationic hemicyanines electrostatic interactions with the underlying PSS⁻ enhances binding of the hemicyanine dyes used in the active control layer to form a stable composite system. PSS⁻ may be impregnated into the pores of Nucleopore polycarbonate membranes (150 Å in pore diameter) by poling, using an electric field of 10 V/cm for one hour from solutions which are approximately $10^{-7}$M in poly(styrene sulfonate). The composite membrane may also be fabricated by direct incorporation of PSS⁻ with hemicyanine LB monolayers by addition of PSS⁻ in the subphase prior to film transfer.

EXAMPLE 3

Permeability as a function of the number of layers was examined. In multilayers constructed from pure, i.e. no stearic acid (SA) diluent, with structures I or II, the permeability was measured from the initial change in fluorescence intensity (in the linear portion of the kinetic curve), as illustrated in FIG. 6. FIG. 6A demonstrates that the trilayer of a 1:9 SA:amphiphile (II) shows a permeability at least a factor of 20 smaller than bare film. It is also roughly an order of magnitude better than the pure monolayer of active amphiphile (not shown). A study of the composition dependence in the low SA concentration regime yielded the results shown in FIG. 7. At least with the structure I amphiphile, there appears to be an optimum film stoichiometry for barrier action in the range of 10–20% SA.

Forward Permeability. We demonstrated the desired control over permeability by constructing a cell in which a moderate voltage (ca. 0–10 V) was applied across a relatively narrow gap (ca. 0.1–1.0 mm) to yield modest fields ($0 \leq E \leq 200$ V/cm). Experiments were performed in an ex situ fashion in which the external solution was first loaded with fluorescein, a convenient probe, which is anionic at the neutral pH values used in these experiments. Then, after exposure to the solution for a given time, the field was applied briefly (2 min. for the results discussed here) in a direction such that electromigration would drive the anionic fluorophore toward the film. FIG. 8 shows the results of the field-induced permeability for films constructed from I:SA and II:SA mixtures as well as the control (E=0) experiments performed in parallel. Clearly the application of a field has a strong effect on the permeability of the probe through the trilayer structure.

Temporal Reversibility. One of the key characteristics of embodiments of the invention is the temporal reversibility of the electric field permeability effect. We have performed measurements of permeability as a function of time with fields on and off. The active layer structure was a trilayer of 80:20 II:SA incorporated into a composite structure composed of a Au/P2VP (ca 1.0 μm)/trilayer. That is, the gold electrode was coated with P2VP. The active layer structure was in the "Z" configuration. Again the experiments were performed in an ex situ geometry, in which the film was physically removed from the apparatus, and the fluorescence intensity of species partitioned into the film measured directly.

What we would expect to see for an ideal film is that there would be no fluorescence increase until the field is applied, followed by an increase in fluorescence while the field is on. Then, when the field is removed the fluorescence would remain constant (due to the fluorophore partitioned into the film during the field-on cycle), and we could then repeat that cycle. If the structural change were not reversible, we would expect to see the fluorescence continue to increase even after the field is turned off. The data are shown in FIG. 9. It is readily evident from the data that after the field is removed the fluorescence remains steady or decreases slightly, indicating that the structural changes are indeed reversible.

Spatial Reversibility. The spatial reversibility of the permeability control effect was demonstrated. We preloaded a P2VP film with fluorophore, and used that loaded film as the substrate for transfer of the active barrier layer. The entire structure was then immersed in a pure H₂O solvent cell. The polarity of the electric field was reversed, and the fluorescein monitored as it leaves the film and is partitioned into the H₂O. The results are given in FIG. 10 where E=30 V/cm and t(E) was 30 seconds for panel A and E=20 V/cm and t(E) was 2 minutes for panel B. The bottom panel B demonstrates the basic spatial reversibility of the effect. However, relatively short (2 minutes) field applications are sufficient to remove nearly all of the fluorophore stored in the film. (A difference between this experiment and the previous ones is that the probe originally resided in the solvent reservoir, and the absolute amount of probe which can be stored in the film experimental modalities is far smaller than that which can be stored in the solvent.) The top panel A of FIG. 10 demonstrates that the application of fields for shorter durations can give temporally reversible back-permeation, i.e. this is the analog of the experiment presented in FIG. 9, however with the polarity of the field reversed and the probe monitored as it is transported out, rather than in. Thus, both the spatial and temporal reversibility of the electric field controlled permeability structures are demonstrated. The magnitudes of the fields used in these latter experiments were of the order of fields used in, for example, electrophoresis.

EXAMPLE 4

Microporous Substrates. This example refers to the Example 2 embodiment. We fabricated a cell which allows us to examine in situ the changes in permeability of such a membrane carrier system, using direct fluorescence excitation of the probes which are transported across the membrane into a receiving reservoir and in which we an apply fields across the membrane of the order $0-10^3$ V/cm. We demonstrated transfer of up to 8 layers in either Y-type or Z-type deposition modes to the membrane. Single membranes are permeable, exhibiting an apparent diffusion coefficient of ca. $10^{-11}$ cm² sec⁻¹. In contrast to the behavior on P2VP, mixed trilayers of II:SA are ineffective, because the LB layers did not span the ca. 150 Å holes in the polycarbonate membrane. Thus, we added a surface layer of poly(styrene sulfonate) to the polycarbonate carrier membrane. The surface layer is put in place by adsorption, which is carried out in the presence of an electric field appropriately polarized to drive the negatively charged PSS⁻ toward the membrane. The detailed preparation of the structure is described in Example 2.

The experiment to test this apparatus was carried out in 0.87 μM rhodamine B, a zwitterionic fluorophore at neutral pH. The PSS⁻ impregnated nuclear-track-etched substrates were covered with a 3 layers of I, and an electric field of 80 V cm⁻¹ was applied. The fluorescence of the receiving solution is shown in FIG. 5. Without the electric field, the receiving solution shows only background fluorescence (the peak near 620 nm is Raman scatter from H₂O), while application of the field results in strong fluorescence from rhodamine B probe molecule transferred to the receiving solution. Since the net charge of the rhodamine B probe under the conditions used is zero, these results do not have an iontophoretic component.

It is to be understood that while the invention has been described above in conjunction with preferred specific embodiments, the description and examples are intended to illustrate and not limit the scope of the invention, which is defined by the scope of the appended claims.

It is claimed:

1. An electric-field responsive assembly useful with target molecules, comprising:

a fluid source with target molecules therein;

a fluid reservoir spaced from the fluid source, the source, and the reservoir defining a fluid passageway therebetween;

a support being interposed in the passageway, the support permitting target molecules to diffuse therethrough; and at least one monomolecular layer carried on a surface of the support, the one and any additional monomolecular layers together forming an active control structure, at least one layer of the active control structure is an admixture of molecular species, at least a majority of the molecular species having a large ground state dipole moment, each monomolecular layer having closely packed, dipolar molecules that are substantially aligned along their long axes, the active control structure having an average off permeability value for target molecules in the absence of an electric field or in the presence of an electric field below a threshold value, the active control structure having an on permeability value to target molecules when at least the electric field threshold value is applied thereacross, the on permeability value being enhanced with respect to the off permeability value.

2. The assembly as in claim 1 wherein the large ground state dipole moment is above about 5 Debye.

3. The assembly as in claim 1 wherein the admixture includes stilbazolium hemicyanines, stilbene derivatives, thiacyanines, oxacyanines, merocyanines, or isocyanines.

4. The assembly as in claim 1 wherein a minority of molecular species are amphiphilics having a carboxyl, alcohol, quaternary amine, or sulfonate head group.

5. The assembly as in claim 4 wherein the minority amphiphilics have up to about 31 carbon atoms.

6. The assembly as in claim 1 wherein each layer has molecules packed so as to be on the order of a short axis molecular diameter of each other in the absence of the electric field threshold being applied thereacross.

7. The assembly as in claim 1 wherein the enhancement is a permeability rate ($cm^2 s^{-1}$) increased by at least about 20 times.

8. An electric-field responsive assembly useful with target molecules, comprising:

a fluid source with target molecules therein;

a fluid reservoir spaced from the fluid source, the source, and the reservoir defining a fluid passageway therebetween;

a support being interposed in the passageway, the support permitting target molecules to diffuse therethrough, the fluid reservoir and support being a composite structure with the composite structure including a swellable polymer, at least one monomolecular layer carried on a surface of the support, the one and any additional monomolecular layers together forming an active control structure, each monomolecular layer having closely packed, dipolar molecules that aligned along their long axes, the active control structure having an average off permeability value for target molecules in the absence of an electric field or in the presence of an electric field below a threshold value, the active control structure having an on permeability value to target molecules when at least the electric field threshold value is applied thereacross, the on permeability value being enhanced with respect to the off permeability value.

9. The electric-field responsive assembly as in claim 8 wherein the support includes a microporous membrane.

10. The assembly as in claim 9 wherein the microporous membrane includes pores with diameters in the range of about 100 Å to about 1000 Å.

11. The assembly as in claim 9 or 10 wherein a polymeric network is disposed between the active control structure and the membrane.

12. The assembly as in claim 11 wherein the polymeric network is bound to the active control structure.

13. A molecular capturing or dispensing device, comprising:

a field-responsive valve unit, the valve unit in fluid communication with a source of target molecules, the valve unit including an active control structure up to about 10 nm thick, the active control structure having at least one monomolecular layer formed by an amphiphilic composition, the amphiphilic composition having a majority of first molecular species with a dipolar moment greater than about 5 Debye, the active control structure being operable in response to an electric field at or about a selected threshold value; and an electrode assembly operably coupled to the valve unit for delivery of an electric field at or above the selected threshold value.

14. The device as in claim 13 wherein the first molecular species includes stilbazolium hemicyanines, stilbene derivatives, thiacyanines, oxacyanines, merocyanines, or isocyanines.

15. The device as in claim 13 or 14 wherein the amphiphilic composition has a minority of second molecular species admixed therein, the second molecular species having fatty acid tails of from about 12 carbons to about 30 carbons.

16. The device as in claim 15 wherein each monomolecular layer of the active control structure has substantially all the amphiphilic composition molecules packed to within about one molecular diameter with respect to a short axis and having substantially all the molecules of the amphiphilic composition being generally aligned with respect to long axes thereof.

17. The device as in claim 15 wherein the monomolecular layers of the active control structure are in a selectable spatial and orientation order.

18. The molecular capturing or dispensing device as in claim 13 wherein a plurality of field-responsive valve units are each operably coupled to at least one electrode assembly.

* * * * *